United States Patent [19]

Miyanaga et al.

[11] Patent Number: 4,808,540
[45] Date of Patent: Feb. 28, 1989

[54] METHOD FOR CHROMATOGRAPHICAL ANALYSIS OF ANIONS

[75] Inventors: Akiyoshi Miyanaga, Yokohama; Masuo Umino, Atsugi, both of Japan

[73] Assignee: Toyo Soda Manufacturing Co., Ltd., Shinnanyo, Japan

[21] Appl. No.: 55,330

[22] Filed: May 29, 1987

[30] Foreign Application Priority Data

May 31, 1986 [JP] Japan ................................. 61-124671

[51] Int. Cl.$^4$ ........................................... G01N 30/14
[52] U.S. Cl. ................................. 436/150; 73/61.1 C; 210/656; 210/198.2; 422/70; 436/161; 436/178
[58] Field of Search .................... 73/61.1 C; 210/656, 210/198.2; 422/70; 436/161, 178, 150

[56] References Cited

U.S. PATENT DOCUMENTS

| | | |
|---|---|---|
| 3,920,397 | 11/1975 | Small et al. |
| 3,925,019 | 12/1975 | Small et al. |
| 3,926,559 | 12/1975 | Stevens |
| 4,451,374 | 5/1984 | Peterson et al. |
| 4,474,664 | 10/1984 | Stevens et al. |
| 4,500,431 | 2/1985 | Miyanaga et al. |
| 4,533,518 | 8/1985 | Hanaoka et al. .................. 422/70 |
| 4,672,042 | 6/1987 | Ross et al. ....................... 436/161 |

OTHER PUBLICATIONS

Small et al.: Novel Ion Exchange Chromatographic Method Using Conductimetric Detection, Analytical Chemistry, (47), 11, Sep. 1975, P1801–P1809.
Fritz et al.: Cation Chromatography with a Conductivity Detector, Analytical Chemistry, (52), 9, Aug. 1980, P1519–P1522.

Primary Examiner—Ivars Cintins
Attorney, Agent, or Firm—Cushman, Darby & Cushman

[57] ABSTRACT

Anions in an aqueous solution can be quantitatively measured at a high sensitivity while controlling the electroconductivity possessed by an eluant to a low level, by the chromatographical analyzing method wherein a separating column, a cation exchange column and an electroconductivity detector are connected in the recited order, an aqueous solution containing an amine compound as an electron donor is used as an eluant, and a cation exchange column composed of the cation exchange resin substituted with a metal ion as an electron acceptor is used as the cation exchange column.

9 Claims, 4 Drawing Sheets

METHOD FOR CHROMATOGRAPHICAL ANALYSIS OF ANIONS

BACKGROUND OF THE INVENTION (1) Field of the Invention

The present invention relates to a method for the chromatographical analysis of anions in an aqueous solution, in which an electroconductivity detector is used.

(2) Description of the Related art

In the conventional chromatographical analysis of anions in an aqueous solution by using an electroconductivity detector, since the S/N ratio of the detector directly reflects the background of the electroconductivity of the eluant, the S/N ratio is reduced as the background is high. Accordingly, where a minute amount of an ion is measured, the S/N ratio should be improved; that is, the background should be reduced. Two different methods are known as means for attaining this object. According to one method, a cation exchange column having a hydrogen ion adsorbed therein is connected downstream from an analysis column for separating an anion in series thereto, the electroconductivity (background) possessed by an eluant is reduced by chemical conversion and, thus, the anion to be measured is detected at a high sensitivity [Small, Stevens and Bauman, Anal. Chem., 47, 1801 (1975)]. According to the other method, an anion is analyzed by using only a separating column without using a cation exchange column and an organic acid such as phthalic acid or tartaric acid is used as the eluant [Fritz, Gjerde and Becker, Anal. Chem., 52, 1519 (1980)].

The principle of the former method using a cation exchange column resides in the utilization of simple ion exchange. A solution containing several mM of sodium hydroxide or sodium hydrogencarbonate and sodium carbonate is used as the eluant, the anion to be measured is separated from the anion exchange resin in the analyzing column, the separated anion is introduced to the cation exchange resin in the cation exchange column having the hydrogen ion adsorbed therein, the sodium ion in the eluant is directly subjected to ion exchange with the restricted hydrogen ion electrostatically connected to the cation exchange resin, and the hydroxyl ion, which is a counter ion to the sodium ion in the eluant, and the carbonic acid ion are chemically converted to water and carbonic acid, respectively, whereby the electroconductivity possessed by the eluant can be controlled to a low level.

This method is expressed by the following chemical reaction formula:

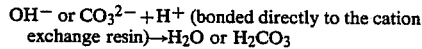

$OH^-$ or $CO_3^{2-} + H^+$ (bonded directly to the cation exchange resin)→$H_2O$ or $H_2CO_3$ As another method utilizing this chemical principle, there can be mentioned a method using a cation exchange membrane instead of the cation exchange column [Hanaoka, Murayama, Muramoto, Matsuura and Nanba, J. Chromatogr., 239, 537 (1982)].

The principle of the latter method using an organic acid as the eluant resides in that since the difference of the electroconductivity between the ion in the eluant and the ion to be measured is reflected on the sensitivity, the electroconductivity possessed by the eluant is controlled to a low level by using as the eluant an organic acid having a low mobility, such as phthalic acid or tartaric acid, rather than an inorganic anion having a high mobility (a high electroconductivity).

As is apparent from the foregoing description, the known methods for the chromatographical analysis of anions by using an electroconductivity detector are based on limited chemical principles, and therefore, development of these methods has been inhibited. Under this background, it is desired to provide an analysis method based on a different chemical principle.

SUMMARY OF THE INVENTION

It is an object of the present invention to provide a method in which an anion to be measured can be quantitatively measured at a high sensitivity while controlling the electroconductivity possessed by an eluant to a low level.

According to the present invention, in the chromatographical analysis of anions in an aqueous solution, a separating column, a cation exchange column and an electroconductivity detector are connected in the recited order, an aqueous solution containing an amine compound which is an electron donor capable of forming a complex with a metal ion is used as an eluant, an anion in a sample is separated in the separating column filled with an anion exchange resin and the separated anion is passed on a cation exchange resin substituted with a metal ion as an electron acceptor in the cation exchange column, whereby the amine compound in the eluant is coordinated with the metal ion through a lone pair of electrons of the amino group and the hydrogen ion on the isolated amino group is chemically bonded to the counter ion of the amine compound to convert the amine compound to a compound having a low conductivity and, thus, reduce the background of the eluant, with the result that the anion to be measured can be detected at a high sensitivity.

DESCRIPTION OF THE PREFERRED EMBODIMENTS

Figure 1:
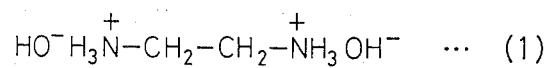
FIG. 1 illustrates the chemical process in the method of the present invention.
Figure 1:
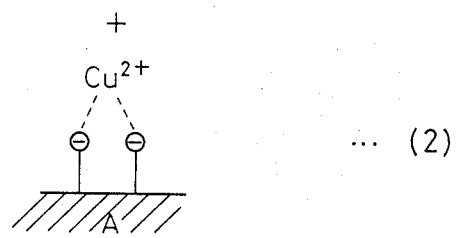
Figure 1:
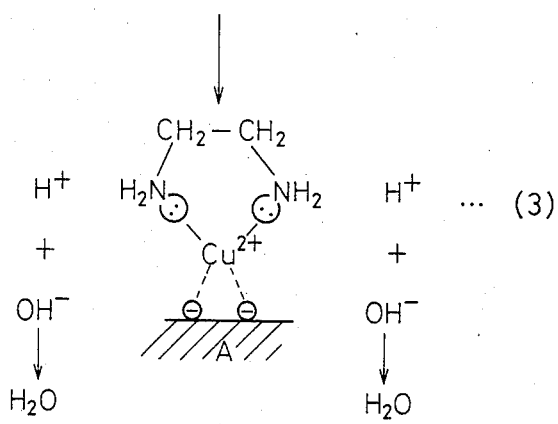

The chemical principle of the method of the present invention will now be described with reference to an embodiment in which an aqueous solution of ethylenediamine is used as the eluant and $Cu^{2+}$ is adsorbed as the metal ion on a cation exchange resin packed in a cation exchange column. The chemical process is expressed by the following formulae shown in FIG. 1. Referring to FIG. 1, the aqueus solution of ethylenediamine which as passed through the separating column does not undergo a chemical change but retains the structure of the formula (1).

When this ethylenediamine comes into contact with $Cu^{2+}$ on the cation exchange resin (A) packed in the cation exchange column expressed by the formula (2), the nitrogen atoms of ethylenediamine are coordinated with the metal ion having a positive charge through a lone pair of electrons to form a complex represented by the formula (3), and simultaneously, the hydrogen ions on the amino groups separate from the nitrogen atoms.

The isolated hydrogen ions are bonded to the hydroxyl ions, which are counter ions of ethylenediamine, by the chemical reaction accompanied by the neutralization of the charge to form water, whereby the electroconductivity of the aqueous solution of ethylenediamine is reduced.

In short, the principle of the present invention resides in a chemical conversion utilizing the coordination of a lone pair of electrons of the amino group with the substituted metal ion on the resin, isolation of the hydrogen ion on the amino group owing to formation of a complex by this coordination and bonding of this isolated hydrogen ion to the counter ion of the amino compound.

The present invention will now be described in detail.

The present invention relates to a method in which the electroconductivity of an eluant is reduced by combining an amine compound in the eluant with a substituted metal ion on a cation exchange resin in a cation exchange column and utilizing the formation of a complex by the amine compound and the metal ion. More specifically, the present invention is characterized in that an amine compound, the counter ion of which has a larger complex-forming constant to the metal ion than the complex-forming constant of the counter ion of the objective anion to the metal ion, is used and a metal ion in which the complex-forming constant of the amine compound to the metal ion is larger than the complex-forming constant of the hydroxide ion, which is the counter ion of the amine compound, to the metal ion is used.

As the objective anion to be measured in the present invention, there can be mentioned inorganic anions such as a fluoride ion, a chloride ion, a bromide ion, a nitrous acid ion, a nitric acid ion and a sulfuric acid ion.

As the amine compound, there can be mentioned ammonia, methylamine, ethylamine, pyridine, ethylenediamine, diethylenetriamine, triaminotriethylamine, triethylenetetramine, propylenediamine, 2,2'-bipyridine, and 1,10-phenanethroline. Among them, ethylamine, ethylenediamine, propylenediamine, diethylenetriamine, triaminotriethylamine, triethylenetetramine, 2,2'-bipyridine, and 1,10-phenanethroline are preferred.

As the metal ion, there can be mentioned iron (III), iron (II), copper (II), nickel (II), cobalt (III), cobalt (II), manganese (II), zinc (II) and mercury (II). Copper (II), nickel (II) and zinc (II) are preferred.

As the eluant to be used in the present invention, there can be mentioned an aqueous solution of an amine compound which is an electron donor. An alkaline aqueous solution containing only an amine compound which is an electron donor is preferred, and an alkaline solution formed by adding boric acid or carbonic acid to the above-mentioned alkaline aqueous solution is especially preferred because the boric acid or carbonic acid ion has a stronger eluting power to the objective anion to be measured than the hydroxide ion which is the counter ion of the amine compound and the measurement time can be shortened. The principle is similar to that represented by the formulae (1) through (3) shown in FIG. 1 and resides in that a lone pair of electrons of the amino group are coordinated with the substituted metal ion on the resin to form a complex, the hydrogen ion on the amino group is isolated by formation of the complex and the isolated hydrogen atom is bonded to the boric acid ion or carbonic acid ion which is the counter ion of the amino compound to effect chemical conversion to boric acid or carbonic acid.

Since the anion exchange resin has an ion exchange capacity of 0.01 to 0.5 milliequivalent/ml, the concentration of the amine compound in the eluant is 0.5 to 20 mM, preferably 1 to 10 mM.

The amount added to boric acid or carbonic acid is not particularly critical, so far as the aqueous solution is kept alkaline. However, it is generally preferred that the molar concentration of boric acid or carbonic acid be equal to or lower than the molar concentration of the amine compound.

The anion exchange resin packed in the separating column is not particularly critical, but an anion exchange resin formed by introducing an amino group into a base such as a polymethacrylate, polystyrene or polyvinyl acetate is generally preferred.

The resin substituted with the metal ion as the electron acceptor, which is packed in the cation exchange column is prepared by washing a cation exchange resin several times with 500 to 50 ml (in total) of an aqueous solution containing a chloride, acetate, nitrate or sulfate of the metal ion at a concentration of 0.05 to 0.5 M. The cation exchange resin to be used is not particularly critical, but bases having an excellent chemical stability to pH, such as polystyrene, a polyacrylate, a polymethacrylate and polyvinyl acetate, are generally preferred. As the ion exchange group to be introduced, there can be mentioned a sulfonic acid group and a carboxyl group, and a sulfonic acid group which has a high electrostatic absorbing property is preferred. The exchange capacity of the resin is not particularly critical. However, a larger exchange capacity is preferred, and an exchange capacity of at least 0.3 meq/ml is especially preferred.

Substitution of the metal on the cation exchange resin can be easily confirmed because the atomic group of the substituted metal ion exhibits a peculiar color. For example, copper (II) and nickel (II) substituted on the cation exchange resin show a light blue color and a light green color, respectively. If these metal ions are coordinated with the amine compound, the colors are changed to violet and blue, respectively. Accordingly, if the above-mentioned cation exchange resin is packed in a transparent or semi-transparent plastic or glass column, the exchange in the cation exchange resin can be easily confirmed based on the change of the hue.

The present invention will now be described in detail with reference to the following examples.

EXAMPLE 1

An apparatus (hereinafter referred to as "apparatus 1") comprising a liquid feed pump [CCPM supplied by Toyo Soda Mfg. Co. (for resins)], a separating column having an inner diameter of 4.6 mm and a length of 5 cm packed with an anion exchange resin (TSK-Gel IC-Anion-PW supplied by Toyo Soda Mfg. Co.) and an electroconductivity detector (CM-8000 supplied by Toyo Soda Mfg. Co.), and an apparatus (hereinafter referred to as "apparatus 2") fabricated by disposing a cation exchange column having an inner diameter of 4.6 mm and a length of 50 mm packed with a cation exchange resin substituted with a copper (II) ion between the separating column and the electroconductivity detector in the apparatus 1, were used.

The cation exchange column in the apparatus 2 was easily constructed by passing 100 ml of 0.2 M copper acetate through a polypropylene column packed with 5 g of a gel of a cation exchange resin having a sodium ion adsorbed thereon [TSK gel SCX supplied by Toyo Soda Mfg. Co. (having a particle size of 10 μm and an ion exchange capacity of 0.4 meq/ml)] and washing the cation exchange resin with 200 ml of deionized water. Electrostatic substitution of the copper (II) ion on the gel was easily confirmed because the light yellowish brown color of the surface of the sulfopropyl group-introduced styrene/divinylbenzene copolymer in the cation exchange resin was changed to a light blue color inherent to the copper-aqua complex. A 2 mM ethylenediamine solution was supplied as the eluant at a rate of 1.2 ml/min, and the electroconductivities of the apparatus 1 and apparatus 2 were measured. It was found that the electroconductivities of the apparatus 1 and apparatus 2 were 180 μS and 2 μS, respectively.

In the apparatus 2, when 5 minutes had passed from the point of initiation of supply of the eluant, a stable base line where the measurement was possible was obtained on a chromatogram. This state was maintained for 10 hours at 2 μS. When the surface of the gel in the ion exchange column was observed through the semi-transparent polypropylene vessel, it was found that the color was changed to violet. Accordingly, it was confirmed that the copper (II)-ethylenediamine complex was formed.

EXAMPLE 2

An aqueous solution containing 1 ppm each of a fluoride ion and a chloride ion was prepared by using sodium fluoride and sodium chloride. By using the apparatus 2, the electroconductivity was measured in the same manner as described in Example 1 while introducing 100 μof the above-mentioned aqueous solution.

Figure 2:
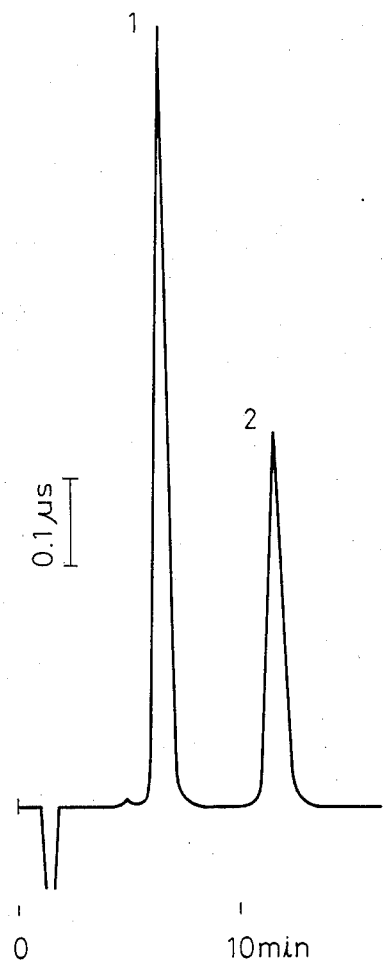
FIG. 2 is a chromatogram obtained according to an embodiment of the present invention.

The obtained chromatogram is shown in FIG. 2. In FIG. 2, reference numerals 1 and 2 indicate a fluoride ion and a chloride ion, respectively.

The coloration of the cation exchange resin was similar to that described in Example 1.

EXAMPLE 3

Figure 3:
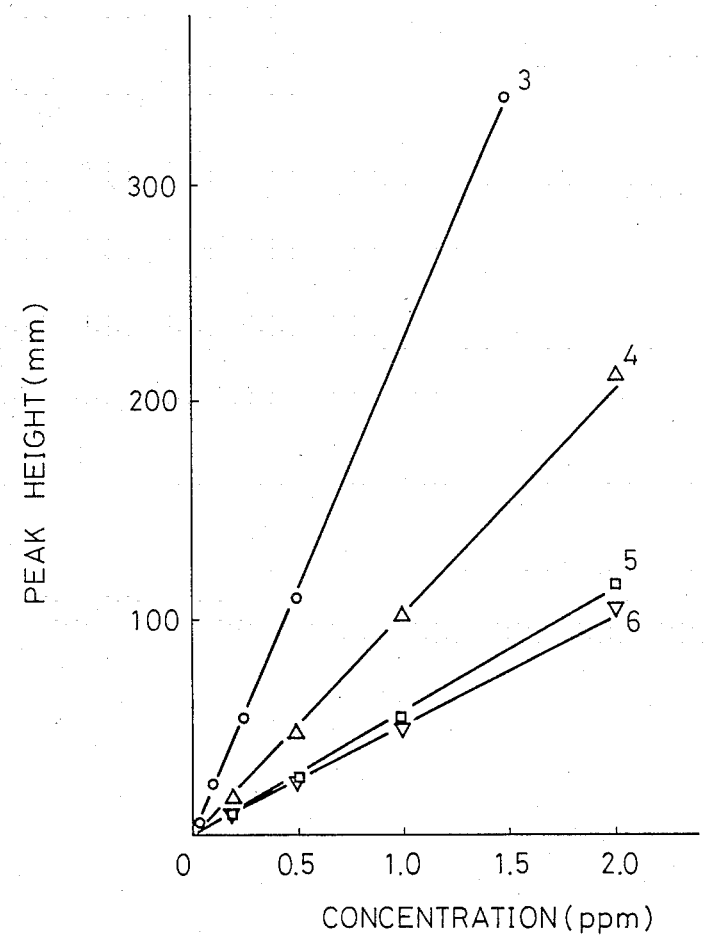
FIG. 3 shows calibration curves of four anions.

Aqueous solutions having different chloride ion, nitrous acid ion, nitric acid ion and bromide ion concentrations were prepared by using sodium chloride, sodium nitrite, potassium nitrate and potassium bromide. With respect to each of the so-obtained aqueous solutions, while 100 μl of the aqueous solution was introduced into the apparatus 2, the electroconductivity was measured in the same manner as described in Example 1 except that an aqueous solution containing 4 mM ethylenediamine and 2 mM boric acid was used as the eluant. Calibration curves of the respective ions were formed based on the obtained measurement results. These calibration curves are shown in FIG. 3. In FIG. 3, reference numerals 3, 4, 5 and 6 indicate calibration curves of a chloride ion, a nitrons acid ion, a nitric acid ion had a bromide ion, respectively. At each run, the coloration of the cation exchange column was similar to that described in Example 1.

Extrapolation values to the origin at respective ion concentrations show a good linearity passing through the origin.

EXAMPLE 4

With respect to each of aqueous solutions containing 3.55 ppm of a chloride ion, 7.99 ppm of a bromide ion, 6.2 ppm of a nitric acid ion and 9.60 ppm of a sulfuric acid ion, the electroconductivity was measured in the same manner as described in Example 1 except that an aqueous solution containing 4 mM propylenediamine and 2 mM carbonic acid was used as the eluant. It was found that the background electroconductivities of the apparatus 1 and apparatus 2 were 221 μS and 13 μS, respectively.

Figure 4:
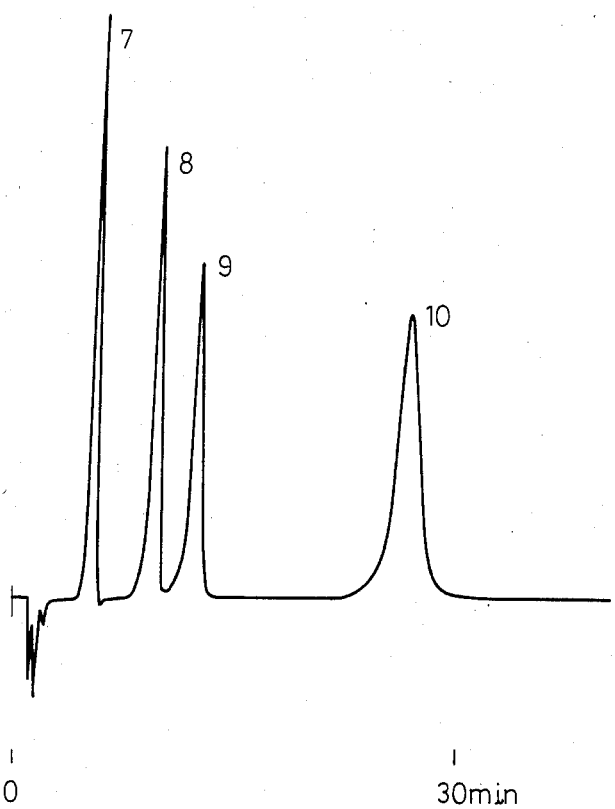
FIG. 4 is a chromatogram obtained according to another embodiment of the present invention.

The chromatogram (20 μS full scale) obtained in the apparatus 2 is shown in FIG. 4. In FIG. 4, reference numerals 7, 8, 9 and 10 indicate a chloride ion, a bromide ion, a nitric acid ion and a sulfuric acid ion, respectively.

As is apparent from the foregoing description, according to the present invention, in the chromatograhical analysis, by using an aqueous solution containing an amino compound as the eluant and passing it through a column packed with a cation exchange resin substituted with a metal ion, which is connected downstream from a separating column in series thereto, the complex-forming reaction between the amino compound and the metal ion is utilized for determining a minute amount of an anion contained in a sample by the measurement of the electroconductivity. Furthermore, although a peak of a nitrous acid ion does not quantitatively appear in a chromatogram obtained according to the conventional analysis method proposed by Small et al, Anal. Chem., 47, 1801 (1975), quantitative determination of a minute amount of a nitrous acid ion can be attained according to the present invention and quantitative determination of various anions can be effectvely performed according to the present invention.

Moreover, since substitution of the metal ion on the cation exchange resin and formation of a complex between the amino compound and the metal ion can easily be confirmed by the change of the color of the resin, the confirmation operation can be simplified.

We claim:

1. A method for the chromatographical analysis of anions in an aqueous solution employing an ion-chromatography system having a separating column, a cation exchange column and an electroconductivity detector, comprising the following steps:

introducing a test sample, which is an aqueous solution containing anions, into the separation column packed with an anion exchange resin while an eluant fluid containing an amine compound as an electron donor is passed through the separation column to separate the anions in the sample and elute the anions from the separation column;

passing the eluant fluid containing the separated and eluted anions from the separation column to the cation exchange column packed with a cation exchange resin substituted with a metal ion as an electron acceptor, to react the amine compound in the eluant fluid with the metal ion to form a complex; and passing the eluant fluid from the cation exchange column to the electroconductivity detector to detect the anions in the eluant fluid;

the counter ion of said amine compound having a larger complex-forming constant to the metal ions than the complex-forming constant of the counter ion of the anions to be analyzed to the metal ion, and said compound having a larger complex-forming constant to the metal ion than the complex-forming constant of the hydroxyl ion, which is the counter ion of the amine compound, to the metal ion.

2. A method for according to claim 1 wherein the eluant is an aqueous solution containing an amine compound and boric acid or carbonic acid.

3. A method according to claim 1 wherein the amine compound is selected from the group consisting of ethylamine, ethylenediamine, propylenediamine, diethylenetriamine, triaminotriethylamine, triethylenetetramine, 2,2'-bipyridine, and 1,10-phenanethroline.

4. A method according to claim 1 wherein the amine compound is ethylenediamine or propylenediamine.

5. A method according to claim 1 wherein the concentration of the amine compound in the eluant is 0.5 to 20 mM.

6. A method according to claim 1 wherein the metal ion is selected from the group consisting of copper (II), nickel (II) and zinc (II).

7. A method according to claim 1 wherein the metal ion is copper (II).

8. A method according to claim 1 wherein the cation exchange resin has an exchange capacity of at least 0.3 meq/ml.

9. A method according to claim 1 wherein the metal ion is selected from the group consisting of iron (III), iron (II), copper (II), nickel (II), cobalt (III), cobalt (II), manganese (II), zinc (II) and mercury (II).

* * * * *